United States Patent [19]

Bucheli

[11] Patent Number: 5,297,599
[45] Date of Patent: Mar. 29, 1994

[54] CLOSURE DEVICE FOR SEALING REAGENT CONTAINERS IN AN AUTOMATIC PIPETTING SYSTEM

[75] Inventor: Rudolf Bucheli, Hünenberg, Switzerland

[73] Assignee: Hoffmann-LaRoche Inc., Nutley, N.J.

[21] Appl. No.: 848,766

[22] Filed: Mar. 10, 1992

[30] Foreign Application Priority Data

Mar. 19, 1991 [CH] Switzerland ................ 823/91

[51] Int. Cl.$^5$ .................. B65D 17/42; G01N 1/10
[52] U.S. Cl. ..................... 141/329; 141/330; 141/18; 215/250; 215/276; 215/307; 215/354; 215/364; 215/DIG. 3; 215/247; 73/864.74; 604/415
[58] Field of Search .......... 73/863.85, 863.86, 864.01, 73/864.14, 864.74, 684.86; 222/80, 81, 85, 86; 141/329, 330, 18, 21, 25-28, 130; 215/247-250, 276, 307, 354, 364, DIG. 3; 604/403, 411, 415

[56] References Cited

U.S. PATENT DOCUMENTS

| | | | |
|---|---|---|---|
| 1,609,387 | 12/1926 | Sweetser | 215/307 |
| 2,689,665 | 9/1954 | Martin | 215/354 X |
| 3,930,413 | 1/1976 | Laird et al. | 73/863.85 |
| 4,022,258 | 5/1977 | Stedley | 141/330 |
| 4,244,478 | 1/1981 | Handman | 215/249 |
| 4,456,138 | 6/1984 | Bereziat | 215/232 |
| 4,796,769 | 1/1989 | Obadia | 215/307 X |
| 4,808,381 | 2/1989 | McGregor et al. | 215/307 X |
| 5,012,845 | 5/1991 | Averette | 141/329 |
| 5,067,532 | 11/1991 | Lang et al. | 141/329 |
| 5,081,872 | 1/1992 | Greter | 73/864.74 |
| 5,088,996 | 2/1992 | Kopfer et al. | 604/415 |
| 5,102,623 | 4/1992 | Yamamoto et al. | 141/130 X |
| 5,202,093 | 4/1993 | Cloyd | 215/249 X |

FOREIGN PATENT DOCUMENTS

| | | |
|---|---|---|
| 24776/77 | 11/1978 | Australia . |
| 35844/78 | 11/1979 | Australia . |
| 53353/79 | 10/1980 | Australia . |
| 0192968 | 9/1986 | European Pat. Off. . |
| 0313010 | 2/1918 | Fed. Rep. of Germany ...... 215/364 |
| 2529531 | 1/1984 | France . |
| 0344759 | 11/1936 | Italy ................ 215/307 |
| 0650458 | 12/1962 | Italy ................ 215/307 |
| WO83/01912 | 6/1983 | PCT Int'l Appl. . |
| 89/04955 | 6/1989 | PCT Int'l Appl. . |
| WO90/06267 | 6/1990 | PCT Int'l Appl. . |
| WO90/09330 | 8/1990 | PCT Int'l Appl. . |

Primary Examiner—J. Casimer Jacyna
Attorney, Agent, or Firm—George M. Gould; George W. Johnston; Robert A. Silverman

[57] ABSTRACT

A closure or cap for a reagent container for use in an analysis system in which an automatic pipetting device is used for transferring small quantities of reagent from the reagent container to reaction cells. In order to simplify the process of handling the reagent container in an automatic analysis system, the closure is characterized in that it is formed in one piece from a plastic and it has a cylindrical side wall and an annular top wall adjacent the side wall and merging into a conical wall which extends inwards from the inner circle of the top wall and ends in a piercable tip situated on the axis of symmetry of the cylindrical wall.

13 Claims, 6 Drawing Sheets

CLOSURE DEVICE FOR SEALING REAGENT CONTAINERS IN AN AUTOMATIC PIPETTING SYSTEM

FIELD OF THE INVENTION

The invention relates to a closure or cap for a reagent container for use in an analysis system in which an automatic pipetting device is used for transferring small quantities of reagent from the reagent container to reaction cells.

The invention also relates to a closure device containing a closure or cap of the type described above.

BACKGROUND

In existing analysis systems, e.g., for clinical chemical analysis of biological specimens, open reagent containers are used. An automatic pipetting device takes a small amount of a liquid reagent from the container and supplies it to a reaction cell. In each pipetting operation, an electromechanically driven arm guides the needle of the pipetting device to a reagent container, guides it in the container so as to remove a volume of reagent, lifts the needle out of the container and guides it to the reaction vessel to which the volume of reagent is to be supplied.

The capacity of a conventional reagent container is sufficient for a relatively large number (of the order of 20 to 2000) of such pipetting operations.

The use of open reagent containers has the following disadvantages:

The laboratory staff has to take each new reagent container out of its packaging, remove the closure and insert the open reagent container into the analysis system in place of an empty reagent container. Often a number of different reagents are needed at different times in the same analysis system. The use of open reagent containers therefore puts the laboratory staff to considerable trouble, because it demands from the staff a considerable amount of work.

When open reagent containers are used in rooms with relatively dry air, some of the reagent solution is lost through evaporation and, consequently, the concentration of the reagent increases with time. Conversely, when open reagent containers are used in rooms with relatively moist air or when water condenses during the use of cooled reagents, the volume of the reagent solution increases and, thus, its concentration decreases with time. Further, when open reagent containers are used, there is also an exchange of gas with the ambient air, and this exchange causes ageing, consequently changing the reagent. All the aforementioned changes in the reagent, particularly in the changes in its concentration, reduce the accuracy of the analisis results. Attempts to obviate this problem by enclosing the entire reagent container in relatively complicated packaging have only been partially effective.

One object of the invention is to provide a closure or cap overcoming these disadvantages.

SUMMARY OF THE INVENTION

According to the invention, the problems mentioned above are solved by a closure or cap characterized in that a) it is formed in one piece from a plastic and
b) it has a cylindrical side wall and an annular top wall adjacent the side wall and merging into a conical wall which extends inwards from the circular aperture in the top wall and ends in a piercable tip situated on the axis of symmetry of the cylindrical wall.

The main advantages of the closure according to the invention are as follows:

For the purpose of pipetting a reagent from the container into the reaction cells, the pipetting needle can be inserted through the closure into the reagent container, it is therefore unnecessary to remove the closure in order to use the container in an analysis system.

In each pipetting process, the conical inwardly extending wall in the central part of the closure guides the pipetting needle through the same place in the closure, i.e. through a small slot in the perforated tip of the conical wall. This ensures that even after a large number of pipetting operations (e.g. 200 to 1000) through the same closure, there is no danger of damage to the closure and no resulting blockage of the pipetting needle (e.g. by fragments of the closure).

Apart from small venting slots, which are open only when the pipetting needle is inserted, a reagent container equipped with the closure according to the invention remains substantially sealed during its entire period of use in the analysis system. This property of the closure according to the invention is a result of its conical wall, which has a shape and length so as to prevent evaporation of the reagent solution, and exchange of gas with the ambient air, and thereby prevents premature ageing of the reagent. As a result the accuracy of the analysis result is increased.

In addition, the closure surrounds and resiliently abuts the pipetting needle at the place of penetration. As a result, the needle is wiped when inserted and pulled out, thus largely preventing contamination by different reagents.

As a result of the advantages obtained using the closure according to the invention the treatment of the reagent container in the analysis system is made more efficient, i.e. the laboratory staff can be relieved of the previously required manual activity.

The closure according to the invention preferably contains a retaining means, for example, a screw cap. This is a simple method of ensuring a efficient seal of the reagent container.

DETAILED DESCRIPTION OF THE INVENTION

The invention will be described in more detail below and where appropriate by reference to the accompanying figures.

One aspect of the invention is a cap member for a reagent container for use in an analysis system with an automatic pipetting device having a pipetting needle for transferring small quantities of at least one reagent from the reagent container to a reaction cell, the cap comprising an outer cylindrical side wall having an inner and an outer surface and having an axis of symmetry parallel to the side wall, an annular top wall perpendicular to the side wall and having a circular aperture, an inner conical wall with an inner and outer surface adjacent to the top wall, having at least two parts, tapering inwardly from the top wall and away from the side wall along the axis of symmetry, and ending at a tip configured and proportioned to be piercable by the pipetting needle, the cap member being formed as a single piece of plastic material.

A preferred embodiment of the closure or cap according to the invention is characterized in that the conical wall has a first part which is adjacent to the top wall and which forms a first angle with the axis of symmetry of the cylindrical side wall, and a second part which forms the tip of the conical wall and which forms a second angle with the axis of symmetry of the cylindrical side wall, said second angle being larger than the first angle. The first angle is preferably between 5° and 30° and the second angle is preferably between 20° and 60°.

In a particularly preferred embodiment the first angle is about 10° and the second angle is about 30°. By this means the conical wall of the closure serves a double purpose in optimum manner, i.e. as a guide for inserting the pipetting needle and as an important part of the closure for tightly sealing the container.

Preferably, access to the conical wall of the closure according to the invention is sealed by a metal sealing foil. As a result the closure has sufficient sealing-tightness for storing freeze-dried or granulated reagents for a prolonged period of time.

A preferred embodiment of the closure according to the invention is characterized in that it has an annular sealing lip adjacent the top wall, the lip being concentric with the side wall and extending inwards and lying between the side wall and the conical wall. This embodiment of the closure has the advantage that it obviates the need for an additional sealing ring between the closure and the container. This embodiment of the closure is particularly suitable for storing reagents in liquid form, because it provides sufficient sealing-tightness over a protracted period of time.

According to the invention, the aforementioned problem is also solved by a closure device characterized in that it contains the following components:
a) a closure made in one piece from a plastic and having a cylindrical side wall and an annular top wall adjacent the side wall and merging into a conical wall which extends inwards from the circular aperture in the top wall and ends in a piercable tip lying on the axis of symmetry of the cylindrical wall, and
b) a sealing means, for example, a plug which is insertable as a seal between the closure and the container and has a central orifice which is adapted to the shape of the outer surface of the conical wall of the closure so that when the container is sealed by the plug and the closure, the outer surface of the conical wall abuts in sealing-tight manner against the inner wall of the orifice through the closure.

Since this closure device contains a closure or cap according to the invention, it provides all the advantages previously described for the closure. The sealing means, exemplified by the plug provided in the closure device, increases the tightness of the seal. This is particularly advantageous for containers holding reagents in granulated form. Preferably all the previously-mentioned embodiments of the closure or cap according to the invention can be used in the closure device according to the invention, except for that embodiment of the closure according to the invention which has an annular sealing lip adjacent the top wall.

An embodiment of the invention will now be described with reference to the accompanying drawings, in which.

Figure 1:
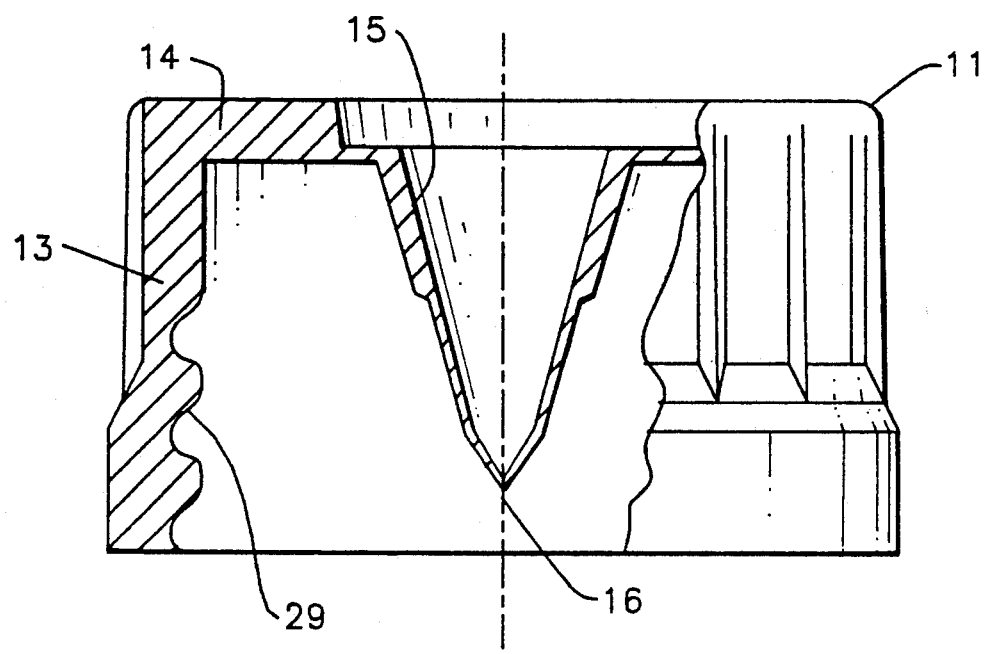
FIG. 1 is a view, partly in section, of a first embodiment of a closure 11 according to the invention.

A first embodiment of a closure or cap 11 according to the invention will now be described with reference to FIGS. 1 and 2. The closure 11 is made in one piece from a plastic. It has a cylindrical side wall 13 and an annular top wall 14 adjacent the side wall and merging into a conical wall 15 which extends inwards from the inner circle or circular aperture of the top wall and ends in a piercable tip 16 which lies on the axis of symmetry of the cylindrical wall, said tip being apt to be pierced e.g. by the pipetting needle of an automatic pipetting device.

Preferably the closure 11 is a screw cap having a side wall 13 formed with an internal thread 29 which matches an outer thread in the neck of the reagent container (not shown) which is to be sealed by the closure.

The conical wall 15 has a first part which is adjacent to the top wall 14 and which forms a first angle with the axis of symmetry of the cylindrical side wall. This first angle is preferably about 10° but can be between 5° and 30°.

The conical wall 15 has a second part which forms the tip 16 of the conical wall and which forms a second angle with the axis of symmetry of the cylindrical side wall 13. This second angle is greater than the first angle. The second angle is preferably about 30°, but can be between 20° and 60°.

Access to the conical wall 15 is preferably sealed by a metal sealing foil 28. An embodiment thereof is shown in FIG. 4.

Figure 2:
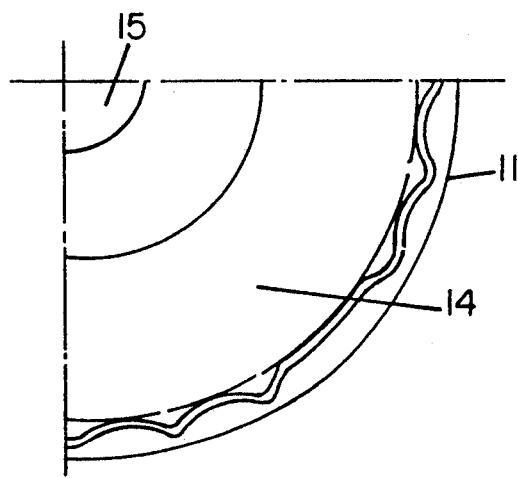
FIG. 2 is a partial top plan view of the closure 11 in FIG. 1.
Figure 3:
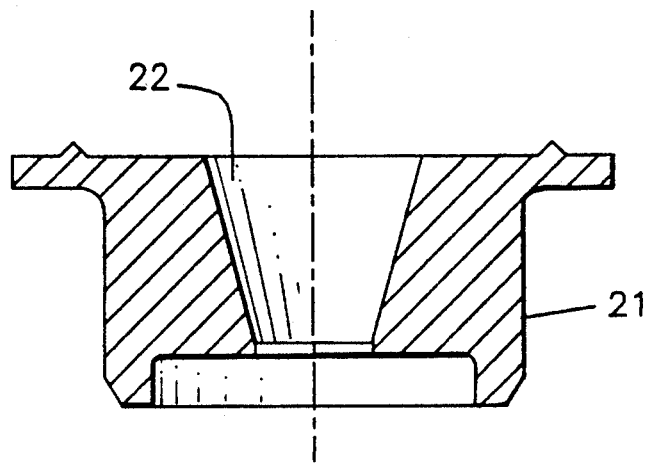
FIG. 3 is a cross-section of a plug 21 adapted to co-operate with the closure 11 in FIG. 1 to form a closure device according to the invention.
Figure 4:
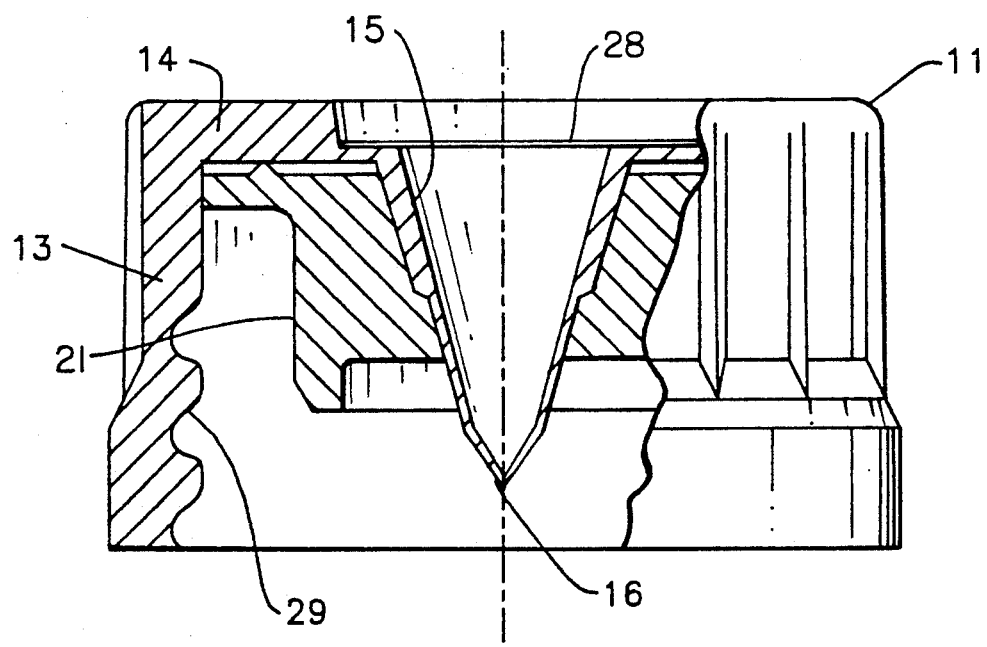
FIG. 4 is a view, partly in cross-section, of a closure device according to the invention.
Figure 5:
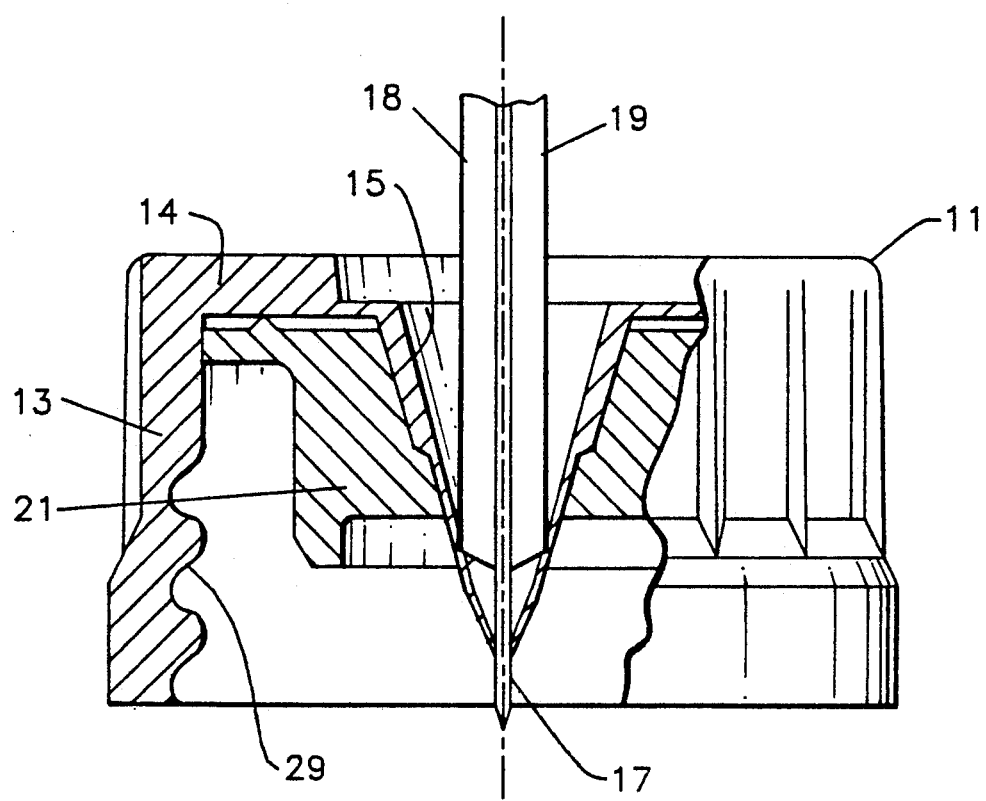
FIG. 5 is a view, partly in cross-section, of the closure device as per FIG. 1 and a spike 17 inserted therein.
Figure 6:
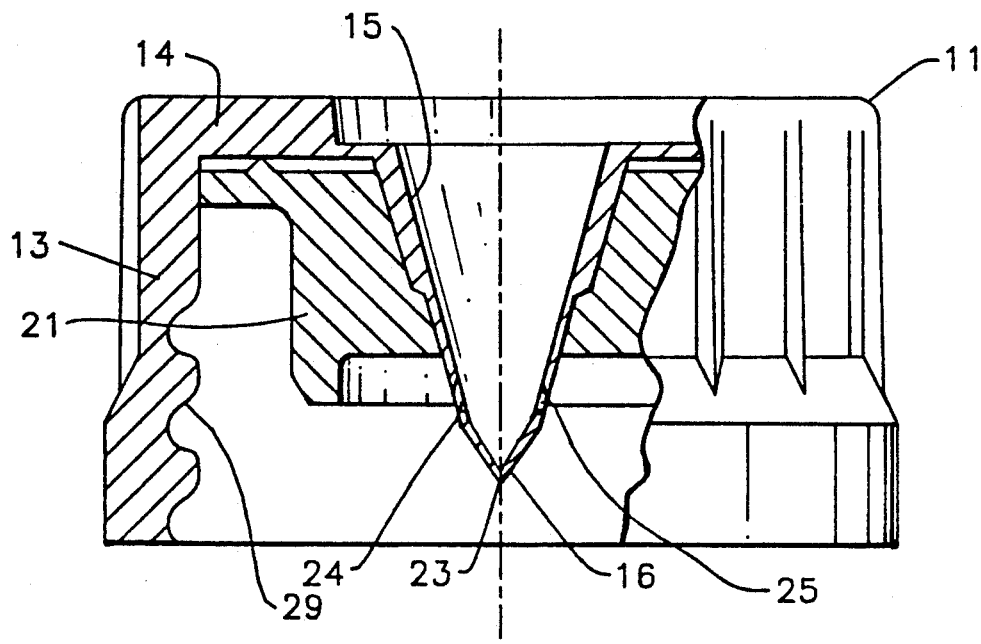
FIG. 6 is a view, partly in cross-section, of the closure device in FIG. 4 after removal of the spike 17 shown in FIG. 5.
Figure 7:
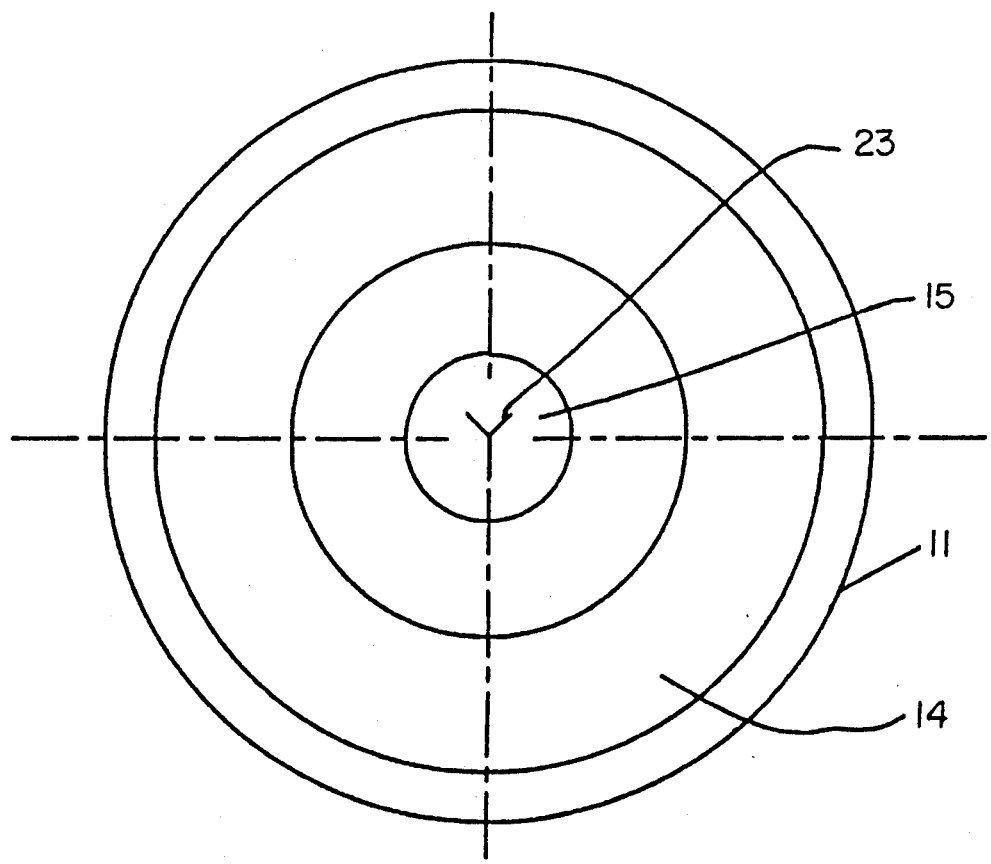
FIG. 7 is a top plan view of the closure device in FIG. 6.

FIG. 3 shows a cross-section through a plug 21 which, in co-operation with the closure 11 in FIG. 1, is adapted to form a closure device according to the invention as in FIG. 4, for providing a particularly good seal.

As FIG. 4 shows, the closure device comprises the previously-described closure or cap 11 and the plug 21, which is insertable as a seal between the closure 11 and the container. The plug 21 has a central orifice 22 which is shaped to match the outer surface of the conical wall 15 of the closure so that when the container is sealed by the plug 21 and closure 11, the outer surface of the conical wall 15 abuts against the inner wall of the orifice 22 through the plug 21 forming a tight seal.

All the embodiments of the closure 11 described with reference to FIGS. 1–4 hereinbefore are suitable for constructing the closure device which has likewise been described.

The use of the closure 11 will be described hereinafter with reference to FIGS. 5–8.

The tip 16 of the conical wall 15 in FIG. 1 is pierced by the tip of a spike 17, which has cutting fins 18, 19. The sharp bottom edges of the fins 18, 19 cut venting slots in the bottom part of the conical wall 15. After the spike 17 has been removed, the conical wall 15 remains in the state shown in FIGS. 6 and 7. A Y-shaped slot 23 is left at the perforated tip of wall 15, and the bottom part of the wall now has venting slots 24 and 25.

Figure 8:
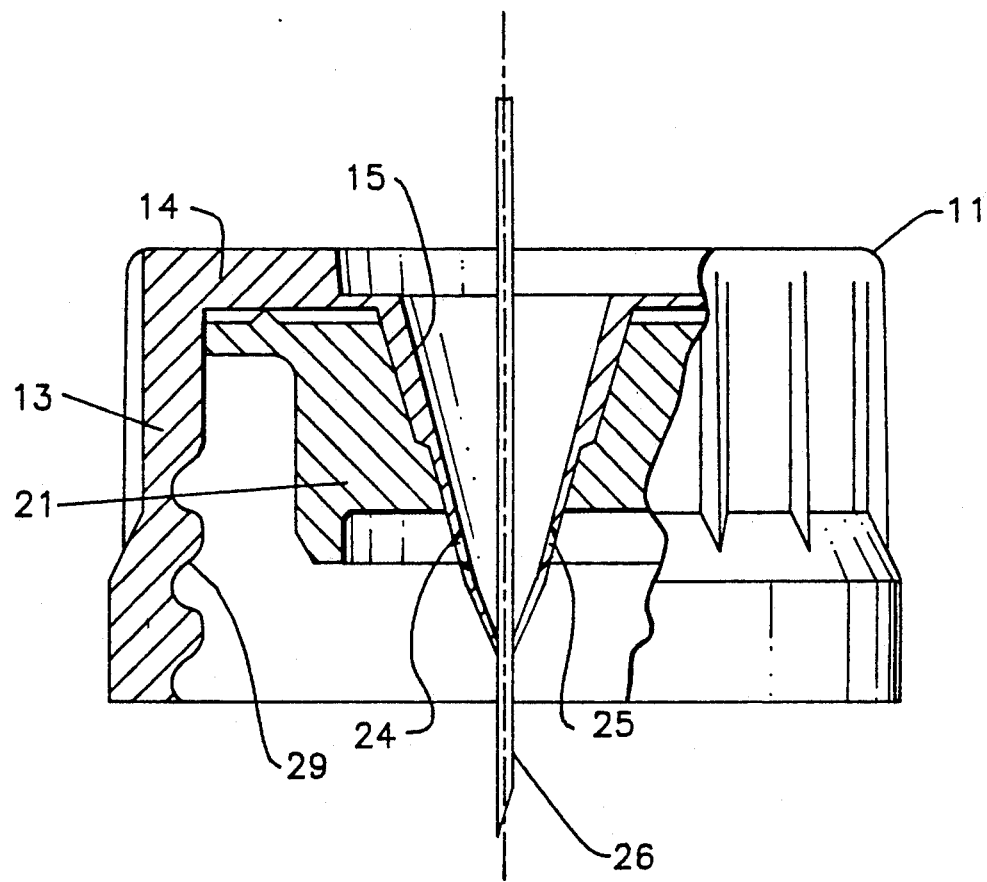
FIG. 8 is a view, partly in cross-section, of the closure device in FIG. 4 and a pipetting needle 26 inserted thereinto.

As shown in FIG. 8, a pipetting needle can now be introduced through the Y-shaped slot at the tip of the conical wall 15 into the reagent container, e.g. in order to remove a given volume of liquid reagent therefrom.

Figure 9:
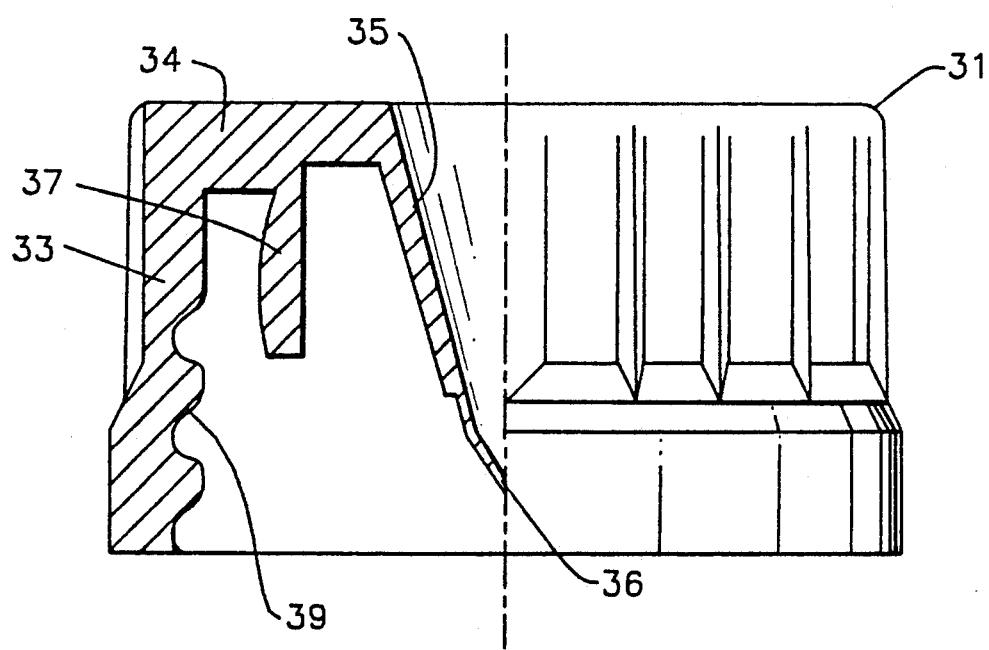
FIG. 9 is a view, partly in cross-section, of a second embodiment of a closure 31 according to the invention.

FIG. 9 shows another embodiment of a closure 31 according to the invention which by itself, i.e. without an additional plug such as the plug 21 in FIG. 4, provides sufficient sealing-tightness for storing a reagent in a container. As before, the closure 31 is made in one piece from a plastic. It has a cylindrical side wall 33 and an annular wall 34 adjacent the side wall and merging into a conical wall 35. The wall 35 extends inwards from the inner circle of the top wall 34 and ends in a piercable tip 36 lying on the axis of symmetry of the cylindrical wall 33. The closure 31 also has an annular sealing lip 37 adjacent the top wall 34, the lip being concentric with the side wall 33, extending inwards and lying between the side wall 33 and the conical wall 35. The side wall 33 of closure 31 is formed with an internal thread 39 which matches an outer thread in the neck of the reagent container (not shown) which is to be sealed by the closure. The neck of the reagent container fits between the annular sealing lip 37 and the side wall 33 in a sealed manner. The embodiment in FIG. 9 is particularly suitable for storing a liquid reagent, e.g. when the required degree of sealing-tightness is not very high. Alternatively, the embodiment in FIG. 4 can be used to store a reagent in dry form (e.g. granulated or freeze-dried), if the required degree of sealing-tightness is ensured by the construction of the closure and particularly by the thickness of its walls.

The use of the closure 11 described with reference to FIGS. 5 to 8 also applies to the closure 31 in FIG. 9.

The closure 11 or 31 is made by injection moulding, e.g. from LD-PE (low density polyethylene). The closure is given a suitable colour, e.g. white.

The plug 21 is made from rubber, for example, bromobutyl rubber.

The sealing foil 28 can be a sandwich foil, i.e. a laminated structure comprising a layer of polyethylene terephthalate (PETP) having a thickness of 12 micrometers, an aluminium layer having a thickness of 12 micrometers and a layer of polyethylene (PE) having a thickness of 100 micrometers.

What is claimed is:

1. A cap member for a reagent container for use in an analysis system with an automatic pipetting device having a pipetting needle for transferring small quantities of at least one reagent from the reagent container to a reaction cell, the cap comprising
   a) an outer cylindrical side wall having an inner and an outer surface and having an axis of symmetry parallel to the side wall;
   b) an annular top wall adjacent to the side wall and having a circular aperture; and
   c) an inner conical wall with an inner and outer surface adjacent to the top wall tapering inwardly from the aperture in the top wall and away from the side wall along the axis of symmetry, and ending at a tip configured and proportioned to be piercable by the pipetting needle,
   the cap member being formed as a single piece of plastic material wherein the inner conical wall has a first and second part, the first part forms a first angle with the axis of symmetry and the second part ending in the tip forms a second angle with the axis of symmetry, the second angle being greater than the first angle, wherein the first angle is about 5° to about 30° and the second angle is about 20° to about 60° with respect to the axis of symmetry.

2. The cap according to claim 1, further comprising a retaining means.

3. The cap according to claim 2, wherein the retaining means comprises an annular screw thread along the inner surface of the side wall.

4. The cap according to claim 1, wherein the first angle is about 10° and the second angle is about 30°.

5. The cap according to claim 1, further comprising a sealing means positioned and configured to cover the circular aperture of the top wall.

6. The cap according to claim 5, wherein the sealing means comprises a metal foil.

7. The cap according to claim 1, further comprising a sealing lip projecting from the top wall and positioned between the side wall and the inner conical wall at a position from the side wall to permit a portion of the container to fit between the lip and the side wall in a sealed manner.

8. A closure device for a reagent container for use in an analysis system with an automatic pipetting device having a pipetting needle for transferring small quantities of at least one reagent from the reagent container to a reaction cell, the closure device comprising
   a) a cap member comprising an outer cylindrical side wall having an inner and an outer surface and having an axis of symmetry parallel to the side wall, an annular top wall adjacent to the side wall and having circular aperture, an inner conical wall with an inner and outer surface adjacent to the top wall tapering inwardly from the aperture in the top wall and away from the side wall along the axis of symmetry, and ending at a tip configured and proportioned to be piercable by the pipetting needle, the cap member being formed as a single piece of plastic material, and
   b) a first sealing means for forming a seal between the cap and the container wherein the inner conical wall of the cap has at least a first and second part, the first forms a first angle with the axis of symmetry and the second part ending in the tip forms a second angle with the axis of symmetry, the second angle being greater than the first angle, wherein the first angle is about 5° to about 30° and the second angle is about 20° to about 60° with respect to the axis of symmetry.

9. The closure device according to claim 8, wherein the cap further comprises an annular screw thread along the inner surface of the side wall.

10. The closure device according to claim 8, wherein the sealing means comprises a plug configured and proportioned to be insertable between the cap and the container, having a central orifice with an inner wall configured to abut the outer surface of the conical wall in a sealing manner.

11. The closure device according to claim 8, wherein the first angle is about 10° and the second angle is about 30°.

12. The closure device according to claim 11, further comprising a second sealing means positioned and configured to cover the circular aperture of the top wall.

13. The closure device according to claim 12, wherein the second sealing means is a metal foil.

* * * * *